United States Patent
Yagi et al.

(10) Patent No.: US 8,598,370 B2
(45) Date of Patent: Dec. 3, 2013

(54) PROCESS FOR PRODUCING THREO-3-(3,4-DIHYDROXYPHENYL)-L-SERINE

(75) Inventors: Toshikazu Yagi, Osaka (JP); Koji Koyama, Osaka (JP); Masanori Itoh, Osaka (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 88 days.

(21) Appl. No.: 13/380,205

(22) PCT Filed: Jun. 29, 2010

(86) PCT No.: PCT/JP2010/061052
§ 371 (c)(1),
(2), (4) Date: Dec. 22, 2011

(87) PCT Pub. No.: WO2011/001976
PCT Pub. Date: Jan. 6, 2011

(65) Prior Publication Data
US 2012/0095256 A1 Apr. 19, 2012

(30) Foreign Application Priority Data
Jul. 1, 2009 (JP) .................... 2009-157360

(51) Int. Cl.
*A61K 31/4166* (2006.01)
*C07D 209/48* (2006.01)

(52) U.S. Cl.
USPC .......................... 548/452; 514/412

(58) Field of Classification Search
USPC .......................... 548/452; 514/412
See application file for complete search history.

(56) References Cited

U.S. PATENT DOCUMENTS

| | | |
|---|---|---|
| 3,920,728 A | 11/1975 | Hegedus et al. |
| 4,330,558 A | 5/1982 | Suzuki et al. |
| 4,497,826 A | 2/1985 | Narabayashi et al. |
| 4,562,263 A * | 12/1985 | Ohashi et al. ............ 548/479 |

FOREIGN PATENT DOCUMENTS

| | | |
|---|---|---|
| JP | 50-49252 | 5/1975 |
| JP | 56-104815 | 8/1981 |
| JP | 58-52219 | 3/1983 |
| JP | 59-216858 | 12/1984 |
| JP | 5-239025 | 9/1993 |
| JP | 8-99940 | 4/1996 |
| JP | 2008-37799 | 2/2008 |

OTHER PUBLICATIONS

Peter G. M. Wuts et al., "Protection for the Amino Group", Greene's Protective Groups in Organic Synthesis, Fourth Edition, 2007, John Wiley & Sons, Inc, pp. 696-700, 790-793, and 799-802.*
International Search Report issued Jul. 27, 2010 in International (PCT) Application No. PCT/JP2010/061052.
Extended European Search Report issued Dec. 6, 2012 in corresponding European Patent Application No. 10794145.2.

* cited by examiner

*Primary Examiner* — Kamal Saeed
*Assistant Examiner* — Janet L Coppins
(74) *Attorney, Agent, or Firm* — Wenderoth, Lind & Ponack, L.L.P.

(57) ABSTRACT

The present invention provides a process for producing Droxidopa or a pharmaceutically acceptable salt thereof comprising a step of reacting threo-N-phthaloyl-3-(3,4-dihydroxyphenyl)-L-serine represented by the formula (1) with methylamine, whereby a process for producing threo-3-(3,4-dihydroxyphenyl)-L-serine (common name: Droxidopa), which is useful as an agent for treatment of peripheral orthostatic hypotension or an agent for treatment of Parkinson's disease, with high production efficiency and without requiring troublesome operations.

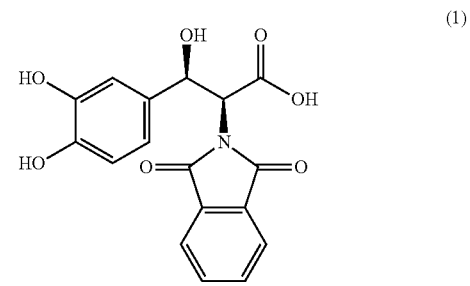

(1)

8 Claims, No Drawings

PROCESS FOR PRODUCING THREO-3-(3,4-DIHYDROXYPHENYL)-L-SERINE

This application is a U.S. national stage of International Application No. PCT/JP2010/061052 filed Jun. 29, 2010.

TECHNICAL FIELD

The present invention relates to a process for producing threo-3-(3,4-dihydroxyphenyl)-L-serine or a pharmaceutically acceptable salt thereof. More specifically, the present invention relates to a process for producing threo-3-(3,4-dihydroxyphenyl)-L-serine or a pharmaceutically acceptable salt thereof comprising a step of reacting threo-N-phthaloyl-3-(3,4-dihydroxyphenyl)-L-serine with methylamine.

BACKGROUND ART

The compound obtained by the present invention, which is represented by the formula (2):

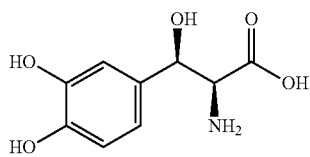

(2)

[chemical name: threo-3-(3,4-dihydroxyphenyl)-L-serine (common name: Droxidopa)], is a drug that has been known to be useful as an agent for treatment of peripheral orthostatic hypotension (see for example, Patent Literature-1) or an agent for treatment of Parkinson's disease (see for example, Patent Literature-2).

As examples of the process for preparing Droxidopa, there has been known a process by reacting a compound represented by the formula (1):

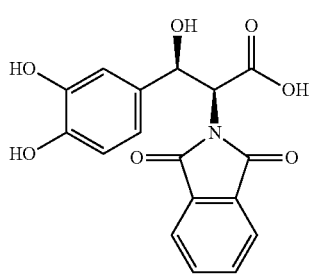

(1)

[chemical name: threo-N-phthaloyl-3-(3,4-dihydroxyphenyl)-L-serine (hereinafter, referred to as "Compound (1)")] with hydrazine (see for example, Patent Literature-3) and a process by removing a protecting group of threo-N-benzyloxycarbonyl-3-(3,4-dibenzyloxyphenyl)-L-serine represented by the formula (3):

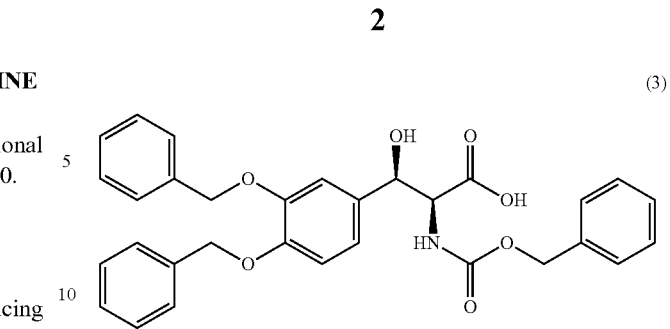

(3)

using a palladium-carbon and the like as a catalyst under a hydrogen atmosphere (see for example, Patent Literature-4) and the like. However, in the case of the former process, there are some problems of requiring a large quantity of reaction solvents because phthalhydrazide as by-product is crystallized and precipitated out, and further requiring some troublesome operations for removing this by-product and additional amounts of the solvents, and the others, and in the case of the latter process, there are some problems of an operation for removing the catalyst used being troublesome, in addition to a process for preparing the above-mentioned compound represented by the formula (3) being troublesome, and these conventional processes thus cannot necessarily be sufficient industrially.

In general, it is known that amines can be used at converting a phthalimido group into an amino group, but there has never been a disclosure that the compound of the formula (1) is reacted with methylamine to obtain the above-mentioned threo-3-(3,4-dihydroxyphenyl)-L-serine represented by the formula (2).

PRIOR ART DOCUMENTS

Patent Documents

[Patent Literature-1]: JP-A S56-104815
[Patent Literature-2]: JP-A S58-52219
[Patent Literature-3]: JP-A H5-20425
[Patent Literature-4]: JP-A S50-49252

DISCLOSURE OF INVENTION

Problems to be Solved by Invention

An object of the present invention is to provide a industrial process for preparing Droxidopa with high production efficiency, characterized by that an amount of solvent used is small and troublesome operations are not also required, as well as to provide Droxidopa that is useful as an active pharmaceutical ingredient of a drug.

Means to Solve Problems

Under such situations, the present inventors have intensively studied to find out a process for preparing Droxidopa with high production efficiency, characterized by that an amount of solvent used is small and troublesome operations are not also required, as a result, they have found that a reaction of the compound (1) with methylamine can produce objective Droxidopa conveniently. That is, the present invention relates to the following embodiments:

[1] A process for producing threo-3-(3,4-dihydroxyphenyl)-L-serine or a pharmaceutically acceptable salt thereof comprising a step of reacting threo-N-phthaloyl-3-(3,4-dihydroxyphenyl)-L-serine with methylamine.

[2] The process for producing threo-3-(3,4-dihydroxyphenyl)-L-serine according to the above [1], wherein the process comprises a step of reacting threo-N-phthaloyl-3-(3,4-dihydroxyphenyl)-L-serine with methylamine.

[3] The process according to the above [1] or [2], wherein the process comprises a step of neutralizing a reaction solution with an acid after a completion of the reaction of threo-N-phthaloyl-3-(3,4-dihydroxyphenyl)-L-serine with methylamine, and a step of isolating the formed threo-3-(3,4-dihydroxyphenyl)-L-serine.

[4] The process according to the above [3], wherein pH after the neutralization is adjusted to a range between 4 and 7.5.

[5] The process according to any one of the above [1] to [4], wherein an amount used of methylamine is 2.1 to 12 times mole based on threo-N-phthaloyl-3-(3,4-dihydroxyphenyl)-L-serine.

[6] The process according to any one of the above [1] to [5], wherein a solvent for the reaction of threo-N-phthaloyl-3-(3,4-dihydroxyphenyl)-L-serine with methylamine is alcohol solvent or mixed solvent of alcohol solvent and water.

[7] The process according to the above [6], wherein the alcohol solvent is methanol.

[8] The process according to the above [6], wherein the solvent is methanol.

[9] The process according to any one of the above [6] to [8], wherein an amount used of the solvent is 0.5 to 3 times in weight based on threo-N-phthaloyl-3-(3,4-dihydroxyphenyl)-L-serine.

[10] The process according to any one of the above [1] to [9], wherein a reaction temperature during the reaction of threo-N-phthaloyl-3-(3,4-dihydroxyphenyl)-L-serine with methylamine is a range between 35° C. and 60° C.

Effect of Invention

The present invention enables to produce Droxidopa using a process with high production efficiency, characterized by that hydrazine or palladium-carbon is not used, an amount of solvent used is small and troublesome operations are not also required, and therefore to provide an industrial production of Droxidopa having high purity at a low price.

MODE FOR CARRYING OUT THE INVENTION

Hereinafter, the embodiments of the present invention are explained in detail.

One embodiment of the present invention is carried out by reacting the compound (1) with methylamine to produce Droxidopa.

Methylamine may be used as either an aqueous solution, a methanol solution, an ethanol solution, a tetrahydrofuran solution or a gas, that is commercially available, and an aqueous methylamine solution that is easy to use is preferred. The amounts used of methylamine can be carried out using 2 to 15 times moles, preferably 2.1 to 12 times moles, more preferably 2.3 to 6 times moles, and further preferably 2.5 to 3.5 times moles based on the compound (1).

The compound (1) can be prepared according to the preparative method described in the above-mentioned Patent Literature-3.

The solvent is not particularly limited unless it can be one that solubilizes methylamine salt of the compound (1), and preferably includes hydrophilic solvents including alcohol solvent such as methanol, ethanol and the others, aprotic polar solvent such as N-methyl pyrolidone, acetone and the others, ether solvent such as tetrahydrofuran, or water alone and mixed solvent thereof, more preferably alcohol solvent or mixed solvent of alcohol solvent and water, and specifically methanol or mixed solvent of methanol and water is preferred and methanol is particularly preferred. The amount used of solvent is not particularly limited, and includes preferably 0.5 to 10 times in weight, more preferably 0.5 to 5 times in weight, yet more preferably 0.5 to 3 times in weight, still preferably 0.75 to 2 times in weight, further preferably 0.75 to 1.5 times in weight, and furthermore preferably 1 to 1.5 times in weight based on the compound (1). Hereinafter, for example, the event of an amount used of solvent being 5 times in weight means an amount used of 5 g solvent based on 1 g compound (1).

The reaction temperature is usually a range between 0° C. and 80° C., preferably a range between 25° C. and 60° C., more preferably a range between 35° C. and 60° C. and further preferably a range between 35° C. and 50° C.

As a sequence at adding methylamine and the compound (1), the compound (1) may be added to methylamine, or reversely, methylamine may be added to the compound (1). They also may be added in a lump sum or may be sequentially or intermittently. The sequential or intermittent addition is preferred due to an easy of removing a heat during the reaction, and further the sequential addition of methylamine to the compound (1) at a constant rate (dropwise addition) is more preferred.

After a completion of the reaction, the reaction solution is neutralized with an appropriate acid to obtain the objective Droxidopa. This operation require neither a treatment of adjusting pH to 1 or less and removing an insoluble material by filtration, nor subsequently a neutralization treatment, in order to remove phthalhydrazide as by-product, as below-mentioned in Comparative Example 1. The acid is not particularly limited unless it is usually a general acid, and preferably includes hydrochloric acid, sulfuric acid, phosphoric acid and the others. The amount used of the acid is not particularly limited unless it is usually sufficient to adjust pH of the reaction solution to the range between 4 and 7.5, and is preferably the amount sufficient to adjust the pH to the range between 4.5 and 6.

After the neutralization, a filtration of the reaction solution and a washing of the filtered materials enable to take Droxidopa out. In order to increase fluidity of the reaction solution or reduce the number of washing, more solvents may be added after the reaction or the neutralization. The solvent to be added may be either the above-mentioned reaction solvent or a mixture thereof.

Droxidopa taken out may be further purified by a usual purification method such as a reverse-phase column chromatography under acidic condition (developed with methanol or acetonitrile and water), a recrystallization from water or mixed solvent of water and hydrophilic solvent such as methanol and ethanol, a neutralization crystallization (once Droxidopa is dissolved in acidic solution of less than 2 of pH or alkaline solution of more than 9 of pH, then the solution is neutralized (adjusted the pH to the range between 4 and 7.5, preferably the range between 4.5 and 6), to precipitate the crystal out).

Droxidopa taken out can form salts thereof by mixing it with an appropriate acid in an appropriate solvent. Example of the solvent includes alcohol solvent such as methanol, ethanol, 2-propanol and the others, aprotic polar solvent such as acetone and the others, ether solvent such as tetrahydrofuran, or water alone and mixed solvent thereof. The amount used of solvent is not particularly limited, and includes preferably 1 to 5 times in weight, more preferably 1 to 2 times in weight based on Droxidopa. Example of the acid that can be used includes inorganic acids such as hydrochloric acid, hydrobromic acid, sulfuric acid, hydroiodic acid, nitric acid and phosphoric acid, or organic acids such as oxalic acid, trifluoroacetic acid, maleic acid, methanesulfonic acid, benzenesulfonic acid and para-toluenesulfonic acid. Preferred acid includes hydrochloric acid, sulfuric acid and phosphoric acid, and the others.

The pharmaceutically acceptable salt of Droxidopa means acid addition salt with the above-mentioned acid. Also Droxidopa and the pharmaceutically acceptable salt thereof may be in a form of hydrate or solvate such as methanol solvate and the others.

EXAMPLES

Hereinafter, the present invention is explained in more detail with some examples, but the present invention should not be construed to be limited thereto. Purity is determined by HPLC external standard method [column: Cadenza CD-C18 (manufactured by Imtakt Corp.), developing solvent: aqueous solution of sodium 1-heptanesulfonate (5 mmol/L) and potassium dihydrogenphosphate (10 mmol/L) (pH 2.0)/acetonitrile=93/7].

Example 1

Threo-N-phthaloyl-3-(3,4-dihydroxyphenyl)-L-serine (30 g) and L-ascorbic acid (0.30 g) were suspended in methanol (30 g), and thereto was added 40% aqueous methylamine solution (20 g) dropwise with stirring at room temperature under nitrogen atmosphere. The reaction solution was stirred at 40° C. for 6 hours and after cooling it to room temperature, it was neutralized with concentrated hydrochloric acid. Thereto were added water (15 g) and methanol (45 g) and after stirring the reaction solution for 1 hour, the reaction solution was filtered and the filtered materials were washed with water and methanol to give threo-3-(3,4-dihydroxyphenyl)-L-serine (16.8 g) (yield: 90.2%). mp 221-223° C. (decomposition) [literature data: 229-232° C. (recrystallization article from water, decomposition), 232-235° C. (recrystallization article from mixed solvent of ethanol and ether, decomposition), refer to Merck Index 14th, Ed.], Purity 98%.

Example 2

Threo-N-phthaloyl-3-(3,4-dihydroxyphenyl)-L-serine (80.0 kg) and L-ascorbic acid (0.86 kg) were suspended in methanol (80.1 kg), and thereto was added 40% aqueous methylamine solution (54.3 kg) dropwise with stirring at room temperature under nitrogen atmosphere. The reaction solution was stirred at 40° C. for 5.6 hours and after cooling it to room temperature, it was neutralized with concentrated hydrochloric acid. Thereto were added water (40.2 kg) and methanol (120 kg) and after stirring the reaction solution for 12.4 hours, the reaction solution was filtered and the filtered materials were washed with water and methanol to give threo-3-(3,4-dihydroxyphenyl)-L-serine (46.1 kg) (yield: 92.9%). Purity 98%.

Example 3

Threo-N-phthaloyl-3-(3,4-dihydroxyphenyl)-L-serine (30 g) was dissolved in mixed solvent of methanol (75 g) and water (15 g) and thereto was added 40% aqueous methylamine solution (20 g) dropwise with stirring at room temperature. The reaction solution was stirred at 40° C. for 9 hours and after cooling it to room temperature, it was neutralized with concentrated hydrochloric acid. After stirring the reaction solution for 1 hour, the reaction solution was filtered and the filtered materials were washed with water and methanol to give threo-3-(3,4-dihydroxyphenyl)-L-serine (17.5 g) (yield: 93.9%). mp 220-222° C. (decomposition). Purity 97%.

Example 4

Threo-N-phthaloyl-3-(3,4-dihydroxyphenyl)-L-serine (30 g) was dissolved in mixed solvent of methanol (30 g) and water (30 g) and thereto was added 40% aqueous methylamine solution (20 g) dropwise with stirring at room temperature. The reaction solution was stirred at 40° C. for 6 hours and after cooling it to room temperature, it was neutralized with concentrated hydrochloric acid. After stirring the reaction solution for 1 hour, the reaction solution was filtered and the filtered materials were washed with water and methanol to give threo-3-(3,4-dihydroxyphenyl)-L-serine (17.0 g) (yield: 91.2%). Purity 97%.

Example 5

Threo-N-phthaloyl-3-(3,4-dihydroxyphenyl)-L-serine [the compound (2)] (30 g) and methylamine (20.4 g) (3 times mole) were stirred in methanol at 40° C. for 6 hours to produce Droxidopa, which was then isolated. Table 1 shows each yield and purity of Droxidopa in various amounts of methanol solvent (times in weight), and residual ratio of reaction intermediate contaminated in Droxidopa isolated, as well as net yield of Droxidopa that is calculated by multiplying the yield of Droxidopa and the purity thereof.

TABLE 1

| | Amounts of methanol | | | |
| --- | --- | --- | --- | --- |
| | 0.5 times in weight | 1 time in weight | 1.5 times in weight | 3 times in weight |
| Yield (%) of Droxidopa | 100.6 | 97.3 | 95.1 | 97.8 |
| Purity (%) of Droxidopa | 91.1 | 97.1 | 96.8 | 95.2 |
| residual ratio (%) of reaction intermediate contaminated in Droxidopa isolated | 0.62 | 0.83 | 1.15 | 2.16 |
| Net yield (%) of Droxidopa | 91.6 | 94.5 | 92.1 | 93.1 |

Reaction intermediate: threo-3-(3,4-dihydroxyphenyl)-N-{[2-(methylcarbamoyl)phenyl]carbonyl}-L-serine In the case that the amount of methanol was 0.5 times in weight, $N^1,N^2$-dimethylphthaldiamide, which was formed by the reaction, was precipitated out, therefore it was observed a reduced stirring efficiency due to an increased viscosity of the reaction mixture, and a reduced purity of Droxidopa due to a contamination of $N^1,N^2$-dimethylphthaldiamide in Droxidopa isolated. Also in the case that the amount of methanol was 3 times in weight, it was observed an increase of the reaction intermediate that was remained in Droxidopa isolated.

Example 6

Threo-N-phthaloyl-3-(3,4-dihydroxyphenyl)-L-serine [the compound of the formula (2)] (30 g) and methylamine (20.4 g) were stirred in methanol (30 g) (1 time in weight) for 6 hours with heating to produce Droxidopa, which was then isolated. Table 2 shows each yield and purity of Droxidopa, and residual ratio of by-product contaminated in Droxidopa isolated, as well as net yield of Droxidopa that is calculated by multiplying the yield of Droxidopa and the purity thereof, in various reaction temperatures.

TABLE 2

|  | Reaction temperatures | | | |
| --- | --- | --- | --- | --- |
|  | 35° C. | 40° C. | 50° C. | 60° C. |
| Yield (%) of Droxidopa | 104.7 | 94.6 | 92.5 | 89.0 |
| Purity (%) of Droxidopa | 87.7 | 97.3 | 99.0 | 98.4 |
| residual ratio (%) of by-product contaminated in Droxidopa isolated | 0.03 | 0.05 | 0.05 | 0.10 |
| Net yield (%) of Droxidopa | 91.8 | 92.0 | 91.6 | 87.6 |

By-Product: Unknown Structure

At 35° C. to 50° C., Droxidopa having good net yield and good quality was obtained, but at 60° C., it was observed an increase of by-product that was remained in Droxidopa isolated and a reduction of net yield.

Example 7

Threo-3-(3,4-dihydroxyphenyl)-L-serine (5.0 g) was suspended in water (7.5 g) and thereto was added concentrated hydrochloric acid (3.8 g) dropwise at room temperature with stirring. The reaction solution was stirred at 60° C. for 30 min., and after cooling it to 0° C. and stirring it for 1 hour, the reaction solution was filtered and the filtered materials were washed with 2-propanol to give threo-3-(3,4-dihydroxyphenyl)-L-serine hydrochloride trihydrate (5.0 g). mp 89-91° C. Purity 100%.

Comparative Example 1

Threo-N-phthaloyl-3-(3,4-dihydroxyphenyl)-L-serine (20.6 g) was dissolved in ethanol (200 mL) and thereto was added 60% aqueous hydazine solution (7.5 g) dropwise at room temperature with stirring, and the reaction solution was heated to reflux for 2 hours. This reaction solution was concentrated under reduced pressure and to the residual was added methanol (200 mL), and the reaction solution was then adjusted pH to 1 or less with concentrated hydrochloric acid. After stirring the reaction solution for 2 hours, insoluble materials were filtered out and the filtered mother liquor was neutralized with 27% aqueous sodium hydroxide solution. The crystal precipitated out was filtered and the filtered materials were washed with methanol to give threo-3-(3,4-dihydroxyphenyl)-L-serine (13.1 g) (yield: 102.4%). mp 211-213° C. (decomposition). Purity 92%.

INDUSTRIAL APPLICABILITY

The present invention is useful as a process for preparing Droxidopa with good production efficiency.

The invention claimed is:

1. A process for producing threo-3-(3,4-dihydroxyphenyl)-L-serine or a pharmaceutically acceptable salt thereof comprising a step of reacting threo-N-phthaloyl-3-(3,4-dihydroxyphenyl)-L-serine with methylamine.

2. A process for producing threo-3-(3,4-dihydroxyphenyl)-L-serine or a pharmaceutically acceptable salt thereof comprising a step of reacting threo-N-phthaloyl-3-(3,4-dihydroxyphenyl)-L-serine with methylamine, and a step of neutralizing a reaction solution with an acid after a completion of the reaction of threo-N-phthaloyl-3-(3,4-dihydroxyphenyl)-L-serine with methylamine.

3. The process according to claim 1, wherein the process comprises a step of neutralizing a reaction solution with an acid after a completion of the reaction of threo-N-phthaloyl-3-(3,4-dihydroxyphenyl)-L-serine with methylamine, and a step of isolating the formed threo-3-(3,4-dihydroxyphenyl)-L-serine.

4. The process according to claim 3, wherein pH after the neutralization is adjusted to a range between 4 and 7.5.

5. The process according to claim 1, wherein a solvent for the reaction of threo-N-phthaloyl-3-(3,4-dihydroxyphenyl)-L-serine with methylamine is alcohol solvent or mixed solvent of alcohol solvent and water.

6. The process according to claim 5, wherein the alcohol solvent is methanol.

7. The process according to claim 5, wherein an amount used of the solvent is 0.5 to 3 times in weight based on threo-N-phthaloyl-3-(3,4-dihydroxyphenyl)-L-serine.

8. The process according to claim 1, wherein a reaction temperature during the reaction of threo-N-phthaloyl-3-(3,4-dihydroxyphenyl)-L-serine with methylamine is a range between 35° C. and 60° C.

* * * * *